United States Patent [19]

Cortes et al.

[11] Patent Number: 5,340,475
[45] Date of Patent: Aug. 23, 1994

[54] ON-LINE SUPERCRITICAL FLUID EXTRACTION MULTIDIMENSIONAL CHROMATOGRAPHIC SYSTEM

[75] Inventors: Hernan J. Cortes; Robert M. Campbell, both of Midland, Mich.

[73] Assignee: The Dow Chemical Company, Midland, Mich.

[21] Appl. No.: 988,950

[22] PCT Filed: Oct. 8, 1991

[86] PCT No.: PCT/US91/07262

§ 371 Date: Mar. 10, 1993

§ 102(e) Date: Mar. 10, 1993

[87] PCT Pub. No.: WO92/05851

PCT Pub. Date: Apr. 16, 1992

Related U.S. Application Data

[63] Continuation of Ser. No. 594,106, Oct. 9, 1990, abandoned.

[51] Int. Cl.$^5$ .............................................. B01D 15/08
[52] U.S. Cl. .................................. 210/198.2; 210/634; 210/635; 210/656; 210/659; 96/101; 96/104; 422/70; 422/83
[58] Field of Search ............... 210/634, 635, 656, 659, 210/198.2; 96/101, 104; 436/161; 422/70, 83; 73/61.52, 61.56, 61.57

[56] References Cited

U.S. PATENT DOCUMENTS

| | | | |
|---|---|---|---|
| 3,686,117 | 8/1972 | Lauer | 210/659 |
| 4,478,720 | 10/1984 | Perrut | 210/659 |
| 4,479,380 | 10/1984 | Novotony | 73/61.1 C |
| 4,500,432 | 2/1985 | Poole | 210/659 |
| 4,597,943 | 7/1986 | Sugiyama | 422/70 |
| 4,775,476 | 10/1988 | Melcher | 210/198.2 |
| 4,793,920 | 12/1988 | Cortes | 210/198.2 |
| 4,806,250 | 2/1989 | Takata | 210/659 |
| 4,913,821 | 4/1990 | Melcher | 210/198.2 |
| 4,935,145 | 6/1990 | Cortes | 210/656 |

OTHER PUBLICATIONS

Wright, B. W., et al, Anal. Chem. 1987, 59, pp. 38–44, Analytical Supercritical Fluid Extraction of Adsorbent Materials.

Anderson, M. R. et al, Chromatogr. Sci., 1989, 27, pp. 371–377, Supercritical Fluid Extraction as a Sample Introduction Method for Chromatography.

Hawthorne, S. B., et al, Chromatogr. Sci., 1990, 28, pp. 2–8, Quantitative Analysis Using Directly Coupled Supercritical Fluid Extraction-Capillary Gas Chromatography (SFE-GC) With a Conventional Split/Splitless Injection Port.

McNally, M. E. P. et al, J. Chromatogr., 1988, 435, pp. 63–71, Supercritical Fluid Extraction Coupled with Supercritical Fluid Chromatography for the Separation of Sulfonylurea Herbicides and Their Metabolites from Complex Matrices.

Xie Q. L., et al, J. Chromatogr., 1989, 27, pp. 365–370, Supercritical Fluid Extraction–Supercritical Fluid (List continued on next page.)

*Primary Examiner*—Ernest G. Therkorn

[57] ABSTRACT

An on-line supercritical fluid extraction multidimensional chromatographic system and method is described which provides a cell for extracting a target compound in a supercritical fluid, and a restrictor interface for trapping the extracted target compound while decompressing and venting the supercritical fluid. A pump and valve arrangement is provided to convey the trapped target compound through a micro LC column for separating (and detecting) constituents of interest from interfering species, and ultimately introducing constituent of interest into a gas chromatograph for analysis. The system is characterized as being "on-line" in that fluid communication is provided between all of the system components and the process is continuous. Similarly, the system is characterized as being "multidimensional" in that both liquid and gas chromatographic techniques can be employed in tandem to provide analysis, selectivity and sensitivity in the parts per billion range.

7 Claims, 2 Drawing Sheets

OTHER PUBLICATIONS

Chromatography with Fraction Collection for Sensitive Analytes.

Hirata, Y. et al, Microcolumn Sep., 1989, 1, pp. 46–50, Supercritical Fluid Extraction Combined with Microcolumn Liquid Chromatography for the Analysis of Polymer Additives.

Unger, K. K. et al, Chromatogr., 1983, 282, pp. 519–526, On–Line High–Pressure Extraction–High–Performance Liquid Chromatography.

Nair, J. B. et al, LC–GC, 1988, 6, pp. 1071–1073, On–Line Supercritical Sample–Preparation Accessory for Chromatography.

Cortes, H. J. et al, J. Chromatogr., 1985, 349, pp. 55–61, Determination of Trace Chlorinated Benzenes in Fuel Oil by On–Line Multidimensional Chromatography Using Packed–Capillary Liquid Chromatograpy and Capillary Gas Chromatography.

Duquet, D. et al, HRC&CC, 1988, 11, pp. 824–829, Coupling Miniaturized Liquid Chromatography to Capillary Gas Chromatography (Micro–LC–CGC): Possibilities of Reversed Phase LC.

Cortes, H. J. et al, Anal. Chem., 1989, 61, pp. 961–965, Multidimensional Chromatography for Polymer Characterization.

Cortes, H. J. et al, HRC&CC, 1987, 10, pp. 446–448, Porous Ceramic Bed Supports for Fused Silica Packed Capillary Columns Used in Liquid Chromatography.

Snyder, "Introduction to Modern Liquid Chromatography" John Wiley & Sons, 1979, pp. 730–731.

Campbell, "Supercritical Fluid Extraction," Journal of Microcolumn Separations vol. I No. 6 (1989) pp. 302–308.

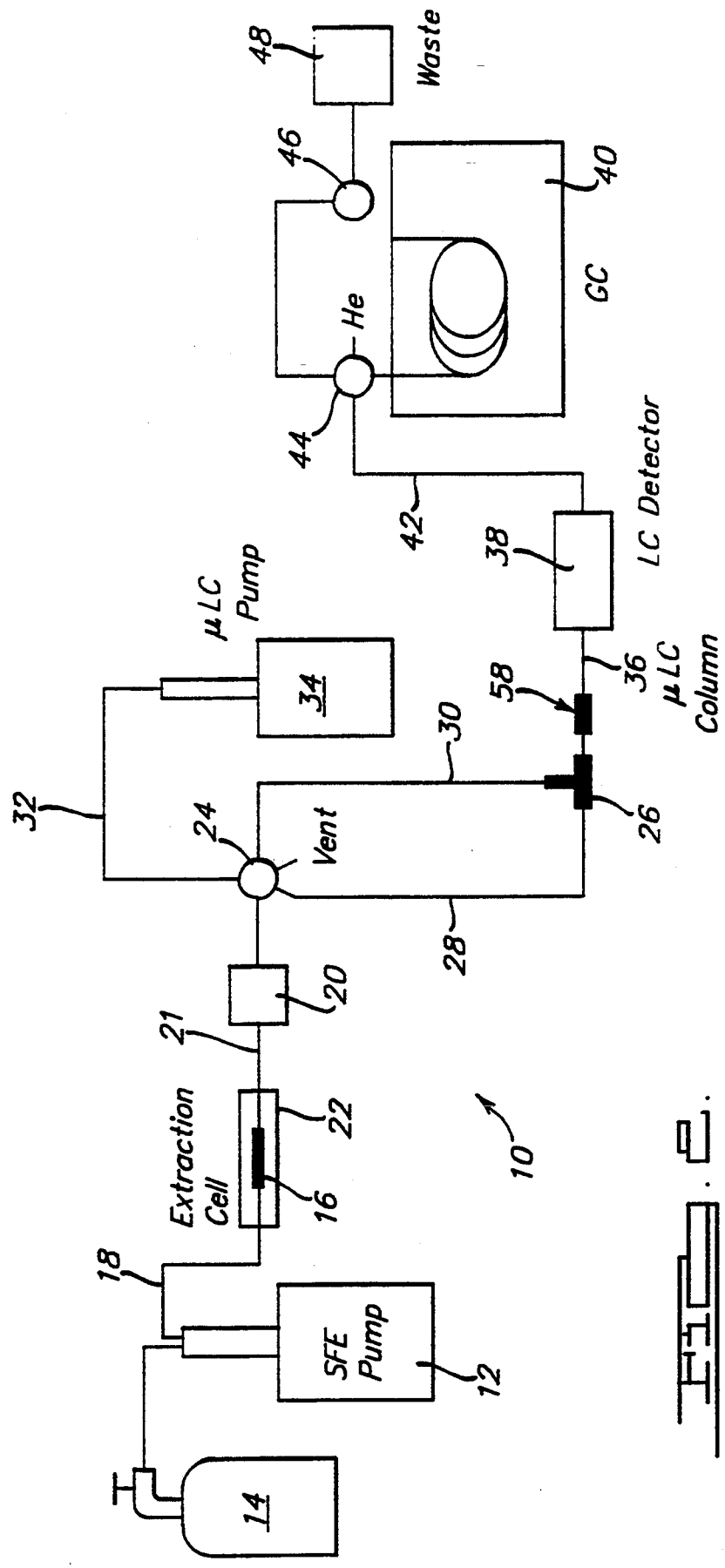

ON-LINE SUPERCRITICAL FLUID EXTRACTION MULTIDIMENSIONAL CHROMATOGRAPHIC SYSTEM

This application is a continuation of Ser. No. 594,106, filed Oct. 9, 1990, now abandoned.

The present invention relates generally to multidimensional chromatography, and in particular to an on-line multidimensional chromatographic system which incorporates supercritical fluid extraction to provide a method and system capable of rapid and efficient sample clean-up and analysis.

In order to analyze target compounds, such as trace pesticides residing on organic matter, substantial preparation is necessary to "clean-up" the sample. By clean-up, it is meant that the trace amount of pesticide or other target compound (e.g., chlorpyrifos) has to first be removed or extracted from the sample before the analysis can be performed. In this regard, a liquid is typically utilized as a solvent to extract the target compound from the sample matter (e.g., a blade of grass). In other words, the target compound is dissolved into the liquid solvent as the initial separation step. However, this procedure has several drawbacks, including the fact that it will be necessary to subsequently separate the extracted target compound from an excessive amount of the liquid solvent.

In contrast, supercritical fluid extraction offers several potential advantages over conventional liquid extraction methods as the initial sample preparation step. In this regard, a supercritical fluid may be defined using a phase diagram such as that shown in FIG. 1 for carbon dioxide. The regions corresponding to the solid, liquid, and gaseous states are well defined. However, at temperatures exceeding the critical temperature ($T_c$), the densities of the liquid and vapor are identical and the fluid cannot be liquefied by increasing the pressure. The shaded area in the phase diagram illustrates the supercritical region. In this region, no phase change occurs, as the fluid is neither a liquid nor a gas. Rather, there is a transition from liquid to supercritical fluid as the temperature is increased at constant pressure, and there is also a transition from gas to supercritical fluid as the pressure is increased at constant temperature.

In general, extractions with supercritical fluids are faster and more efficient than conventional liquid or soxhelet extraction methods. Supercritical extraction is based upon the solubility of the target compound in the supercritical fluid, and this solubility property can be changed by varying the density of the particular supercritical fluid. In other words, a low density supercritical fluid approaching the qualities of a gas will typically not be as good an extraction fluid as one that approaches the densities of a liquid. Thus, the extraction strength of the supercritical fluid may be controlled by adjusting its density, which is in turn controlled by the temperature and pressure of the fluid. For example, because the compressibility of a supercritical fluid is large above the critical temperature, small changes in the pressure applied to the fluid will result in large changes in the density of the fluid.

Supercritical fluid densities can be two to three orders of magnitude larger than those of the gas. As a result of this larger density, molecular interactions in supercritical fluids increase due to shorter intermolecular distances. On the other hand, the viscosity and mass transport properties of supercritical fluids remain similar to those of a gas. The gas-like/liquid-like quality of supercritical fluids allow similar solvent strengths as liquids along with improved mass transport. Since supercritical fluids offer these two properties simultaneously, they provide the potential for rapid extraction rates and more efficient extractions. A further discussion of supercritical fluid extraction may be found in "Supercritical Fluid Extraction of Chlorpyrifos Methyl from Wheat at Part per Billion Levels", by Robert M. Campbell, David M. Meunier and Hernan J. Cortes, in the Journal of Microcolumn Separations, Volume I, No. 6, 1989, pages 302–308.

While supercritical fluid extraction ("SFE") offers several potential benefits as a tool to recover target compounds from complex sample matter, its utility would be substantially enhanced if an on-line, SFE based, multidimensional chromatographic system could be created with an accuracy level in the parts per billion ("ppb") range. The achievement of such a system could provide a continuous method of extracting, separating and analyzing selective constituents of interest from target compounds containing a variety of interferences. In this regard, certain interferences may not be apparent when an analysis is conducted in the parts per million ("ppm") range, and the capability of separation and resolution in the ppb range would be particularly advantageous.

Accordingly, it is a principal objective of the present invention to provide an on-line supercritical fluid extraction multidimensional chromatographic system and method of sample preparation and analysis which will enable a rapid, reliable and precise analysis to be made of selected constituents of interest in the ppb range.

It is a more specific objective of the present invention to provide an on-line supercritical fluid extraction multidimensional chromatographic system and method which extracts the target compound, separates one or more constituents of interests from the target compound by liquid chromatography and then analyzes these constituents of interest by gas chromatography in a continuous process which is capable of automation.

It is also an objective of the present invention to provide an interface for the system which is capable of trapping an extracted target compound with a minimum of spreading while decompressing and venting the supercritical fluid.

To achieve the foregoing objectives, the present invention provides an on-line supercritical fluid extraction multidimensional chromatographic system which includes a cell for extracting a target compound in a supercritical fluid, a restrictor interface for trapping the extracted target compound while decompressing and venting the supercritical fluid, a valve arrangement for enabling a carrier fluid to convey the trapped target compound through a liquid chromatographic ("LC") column, and a gas chromatograph for analyzing selected constituents of interest eluting from the LC column in a continuous process.

In one embodiment according to the present invention, the restrictor interface includes an impactor in the form of a capillary-based porous ceramic frit for trapping the extracted target compound during the decompression of the supercritical fluid. A valve is also provided to prevent flow through the LC column when the extracted target compound is being trapped in the restrictor interface. These provisions serve to control the precipitation of the extracted target compound and subsequent introduction into the LC column, so that relatively sharp chromatographic peaks will be produced by the LC and GC detectors.

BRIEF DESCRIPTION OF THE DRAWINGS

Additional advantages and feature of the present invention will become apparent from a reading of the detailed description of the preferred embodiment which makes reference to the following set of drawings in which:

FIG. 2 is a block diagram of an on-line supercritical fluid extraction multidimensional chromatographic system according to the present invention.

DESCRIPTION OF THE PREFERRED EMBODIMENTS

Figure 1:
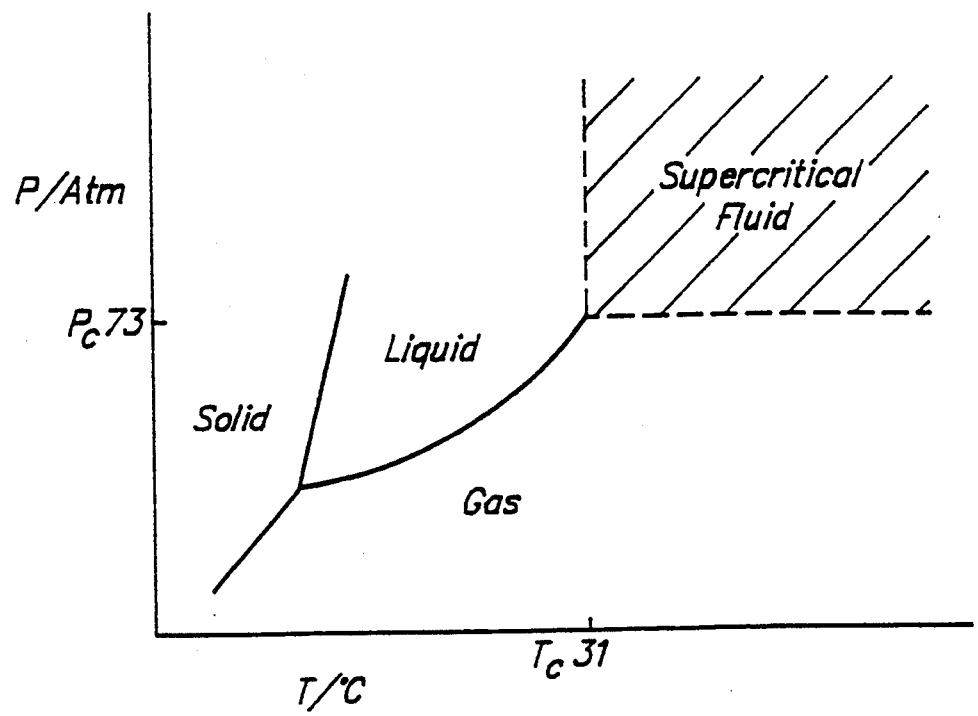
FIG. 1 is a phase diagram of carbon dioxide for illustrating the supercritical fluid range of one exemplary fluid capable of being utilized in the present invention.

Referring to FIG. 1, the phase diagram for carbon dioxide is shown to illustrate its usefulness as a supercritical fluid. In this regard, carbon dioxide is relatively inexpensive, readily available, and has critical temperature and pressure properties which make it easy and practical to use in the supercritical region. However, one of the disadvantages of carbon dioxide is its lack of polarity at a molecular level. Accordingly, other fluids may be added to carbon dioxide, such as methanol, in other to provide a supercritical fluid mixture for extracting more polar materials or compounds in the appropriate application. Additionally, it should be appreciated that other fluids (e.g., ammonia, acetonitrile, tetrahydrafuran) may be used alone or in combination with other fluids to provide a supercritical fluid which is suitable for extracting the target compound under investigation.

Referring to FIG. 2, an on-line supercritical fluid extraction multidimensional chromatographic system 10 according to the present invention is shown. The system 10 includes a syringe pump 12 which receives fluid from a suitable source, such as a liquid carbon dioxide cylinder 14 (having supercritical fluid chromatography grade carbon dioxide with 2% methanol). The syringe pump 12 is used to pump fluid (previously loaded as a batch process) from source 14 at a pressure in the supercritical range, (so that the fluid from source 14 will be delivered as a supercritical fluid). In one form of the present invention, the syringe pump 12 is a Varian 8500 syringe pump from Varian Instruments, Sunnyvale, Calif. While this syringe pump permits manual control of the pressure (and hence the density) of the supercritical fluid, this pump may be commercially modified to permit pressure control via a computer. Alternatively, computer controlled packages are available, such as the Model 501 supercritifcal fluid chromatograph from Dionex/Lee Scientific, Inc. While the flow rate of the pump 12 will vary with pressure/density, the flow rate may be measured by determining the volume of fluid flowing through the system over time. When carbon dioxide is used as the supercritical fluid, the preferred pressure range of operation is generally between 500 and 6000 psi (3–40 MPa). Preferably, the pressure is increased from an initial value (e.g., 100 atm. (10 MPa)) to a final constant value (e.g., 400 atm. (40 MPa)) over a suitable period (e.g., 6 min.) to increase the density in order to promote solvation and extraction of desired components. Similarly, the preferred flow rate produced by the syringe pump 12 is generally between 20 and 100 microliter/min.

The system 10 also includes an extraction cell 16 which is connected to the output of the syringe pump 12 via transfer conduit 18. The extraction cell 16 is used to hold a sample which has a target compound or component that is soluble in or otherwise capable of being removed from the sample by the supercritical fluid being delivered to the extraction cell. Accordingly, the extraction cell 16 enables the target compound to be extracted or removed from the sample by the washing action of the supercritical fluid. In order to prevent any possible plugging of the downstream transfer conduits as a result of this washing action, a filter media 20 may be coupled to the outlet of the extraction cell 16.

In one form of the present invention, each of the transfer conduits/lines, such as transfer conduit 21, are preferably made of fused silica (e.g., 375 $\mu$m o.d.$\times$50 $\mu$m i.d.). Additionally, the extraction cell 16 may be a stainless steel "T-series" tube (1.0 cm$\times$4.6 mm i.d.) from Keystone Scientific, Bellefonte, Pa. This extraction vessel is preferably equipped with polyetheretherketone (PEEK)-collared, 0.5 $\mu$m pore size, stainless steel frits to seal the tube. The filter media 20 is preferably a porous ceramic plug which is contained in the transfer conduit 21 connected to the outlet of the extraction cell 16. In this regard, the porous ceramic plug may be cast in situ in accordance with the method described in U.S. Pat. No. 4,793,920.

The extraction cell 16 is contained in an oven 22 to control the temperature at which the extraction process will take place. The oven 22 includes model TC-50 HPLC column heaters and a model CH-30 temperature controller from FIAtron Systems, Oconomowoc, Wis. When carbon dioxide is used as the supercritical fluid, the preferred temperature range of operation is generally between 40 and 150 degrees celsius, with 100° C. being the most preferred.

A multi-port switching valve 24 is coupled to the outlet of the extraction cell 16 to control the direction of fluid flow from the extraction cell. In one embodiment according to the present invention, the valve 24 is a Valco ten port valve, model NI10WT, from Valco Instruments, Houston, Tex. In the extraction mode, the valve 24 couples the output of the extraction cell 16 to a restrictor interface 26 via transfer conduit 28 (e.g., a fused silica restrictor, 25 $\mu$m i.d.$\times$150 $\mu$m o.d.). In this mode, the extracted target compound or analyte will be conveyed with the supercritical fluid from the extraction cell 16, through the valve 24 and into the restrictor interface 26.

The restrictor interface 26 is used to trap the extracted target compound while enabling the supercritical fluid to decompress and be vented back through the valve 24 via transfer conduit 30. The internal diameter of the transfer conduit 30 should not be too small, as the pressure increase may cause the decompression to occur in the conduit, rather than in the interface. In one form of the present invention, the transfer conduit 30 has an internal diameter of 250 $\mu$m and the vent tube leading from the valve 24 has an internal diameter of 320 $\mu$m.

The restrictor interface 26 separates the extracted target compound from the supercritical fluid by decompressing the supercritical fluid into an escaping gas and precipitating or depositing the target compound in a confined location. In this regard, the difficult goal to be achieved is the provision of a construction and method of operation which will control the decompression of the supercritical fluid, efficiently trap the target compound and ultimately produce narrow bandwidth chromatographic peaks in a continuous and repeatable procedure. A discussion of the restrictor interface construction will be presented in connection with FIG. 3.

Once the extracted target compound has been trapped by the restrictor interface, the valve 24 is switched to the analysis mode. In the analysis mode, the valve 24 places transfer conduit 30 in fluid communication with a transfer conduit 32 which is connected to a micro liquid chromatograph pump 34, and the valve 24 blocks or cuts off flow through transfer conduit 28. The micro LC pump 34 is used to deliver a carrier fluid or solvent (e.g., 85:15 acetonitrile/water) to the restrictor interface 26 through transfer conduits 30 and 32. In one form of the present invention, the pump 34 is an Isco u - LC 500 solvent delivery system from Isco, Lincoln, Neb., operated at a constant flow rate and pressure (e.g., 6 $\mu$L/min at 1750 psi (12 MPa)).

Solvent flow from the pump 34 will wash the deposited target compound from the restrictor interface 26 and cause this analyte to pass through a micro LC column 36 which is connected directly to the restrictor interface. The micro LC column 36 will separate one or more constituents of interest (e.g. Chlorpyrifos) from the various interferences (e.g. grass extractables) to effect a clean-up procedure and permit detection of these constituents of interest by LC detector 38. In other words, the micro LC column 36 enables the constituents of interest to be separated from various interferences which would otherwise cause an overly complex gas chromatogram. Additionally, this separation also makes it possible to substantially increase the resolution of the gas chromatogram so that the constituents of interest may be detected and analyzed in the parts per billion ("ppb") range. In one form of the present invention, the micro LC column 36 is a 30 cm long 250 $\mu$m i.d. $\times$ 400 $\mu$m o.d. coated fused silica column packed with spherisorb ODS of 5 $\mu$m particle diameter, and the LC detector is a model UV1DEC V detector from Jasco Inc., Japan. However, it should be appreciated that this micro LC column and LC detector combination is intended to be exemplary, and that these and other exemplary components described herein may be modified or replaced with other suitable components in the appropriate application.

The effuent eluting from the micro LC column 36 is conveyed to a gas chromatograph 40 via transfer conduit 42. However, a pair of valves 44 and 46 are used to control the fluid flow from the micro LC column 36, so that the constituents of interest may be directed into the gas chromatograph 40 at the appropriate time for further separation and quantitation. Specifically, switching valve 44 is interposed between transfer conduit 42 and the gas chromatograph to control the introduction of the effluent into the gas chromatograph, while on/off valve 46 is coupled to the valve 44 to permit or prevent flow through the micro LC column 36 at all. In other words, valve 44 either directs fluid flow into the gas chromatograph 40 or directs fluid flow onto valve 46. When valve 46 is closed and valve 44 is directing fluid flow to valve 46, fluid flow through the micro LC column 36 is blocked. This condition is employed during the extraction mode when it is desirerable to prevent or minimize fluid flow through the micro LC column 36. Then, during the analysis mode, valve 46 is opened to allow fluid flow from the micro LC column 36 to waste collection vessel 48. After the region containing the constituents of interest has been detected by LC detector 38, the valve 44 is switched to introduce this region of fluid flow into the gas chromatograph 40.

In one form of the present invention, the gas chromatograph 40 is a model 5890 GC from Hewlett-Packard, Bellafonte, Pa., USA. This particular gas chromatograph is equipped with an electron capture detector which will generate a chromatogram for analyzing the constituents of interest separated by the micro LC column 36. With respect to the conditions of operation, the temperature of the GC oven is preferably set initially to 120° C., and then when the process begins, the oven temperature should be set to rise 8° C./min. until 280° C. is reached. Additionally, Helium is preferably used as the carrier fluid at 10–40 psi (70–280 kPa). Other preferred GC operating conditions are an initial oven temperature which allows some degree of solvent evaporation to occur (e.g. 40 degrees celsius to 150 degrees celsius dependent on effuent used) and temperature program rates of 2° C./min to 32° C./min.

Figure 3:
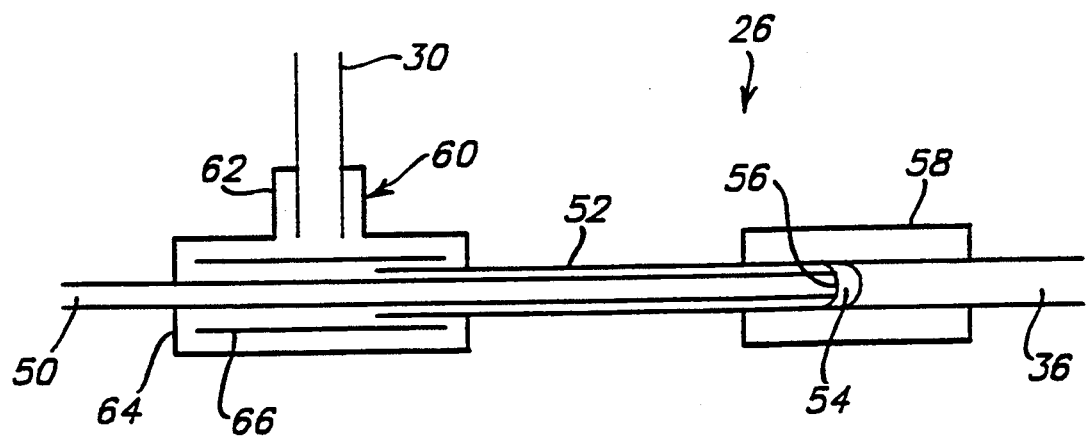
FIG. 3 is a diagrammatic representation of the restrictor interface shown in FIG. 2.

Referring to FIG. 3, the restrictor interface 26 is shown to include a restrictor conduit 50 which is coaxially disposed in a transfer conduit 52. Both the restrictor conduit 50 and the transfer conduit 52 are preferably fused silica capillaries from Polymicro Technologies, Phoenix, Ariz., USA. In the case of the restrictor conduit 50, the inner diameter is preferably in the range between 10 $\mu$m and 25 $\mu$m in order to cause the supercritical fluid to decompress slowly while the outer diameter is closely related to the inner diameter of the transfer conduit 52. For example, with an outer diameter of 195 $\mu$m for the restrictor conduit 50, the inner diameter of the transfer conduit should be approximately 200 $\mu$m. Similarly, for a restrictor conduit having an inner diameter of 15 $\mu$m and an outer diameter of 150 $\mu$m, the inner diameter of the transfer conduit should be 200 $\mu$m with an outer diameter of 350 $\mu$m. In other words, the inner diameter of the transfer conduit 52 should be the smallest size commercially available that is still large enough to permit the restrictor conduit to slide into and be held by the transfer conduit 52 without otherwise providing support between the restrictor conduit and the transfer conduit. This very small inner diameter for the restrictor conduit 50 provides sufficient back pressure in the system so that the pressure of the supercritical fluid flow through the extraction cell may be controlled by the syringe pump 12. Additionally, it should be noted that the close fit between the restrictor conduit and the transfer conduit may assist in reducing possible band broadening. As for the length of the restrictor and transfer conduit sections, the transfer conduit 52 need only be long enough to permit the connections at each end to be made (e.g., 3 cm). In contrast, the length of the restrictor conduit 50 should be long enough to assist in controlling the decompression of the supercritical fluid (e.g., 15–20 cm).

As shown in FIG. 3, the restrictor interface 26 also includes an impactor 54 for trapping the target compound as the supercritical fluid decompresses into a gas and escapes back through the transfer conduit 52. In this regard, the impactor 54 is used to dissipate any kinetic energy that may be present during the decompression of the supercritical fluid, and provide a surface upon which the target compound may be deposited or precipitated. Specifically, the impactor 54 should be constructed to minimize excessive travel or spreading of the target compound, so that narrow/sharp chromatographic bands may be introduced into the liquid chromatograph. In one form of the present invention, the impactor 54 is a porous ceramic frit formed in situ at the end of the transfer conduit 52 according to U.S. Pat. No. 4,793,920. As discussed more fully in this patent, the end of the transfer conduit 52 is dipped into liquid potassium silicate with a catalyst, and capillary action is allowed to bring the liquid into the tube (e.g., 0.1-1.0 mm). The tube is then heated to polymerize the material to create the frit with a porosity on the order of 5,000 angstroms (500 nm) and cut to a desired length. Since the impactor can be subjected to large pressure changes when the valves 24 and 48 are switched, the frit length must be long enough (e.g., 1.0 mm) to provide mechanical stability in the transfer conduit 52. While the impactor 54 could be comprised of a solid block of material (e.g., quartz) disposed at or press fitted into the end of the transfer conduit 52 (leaving gaps for fluid flow), such a construction is not considered to be as effective as a cast in situ porous ceramic frit in terms of concentrating the precipitation of the target compound in a limited area.

It should also be noted that in this preferred embodiment, the decompressed supercritical fluid reverses the direction of its linear flow as it travels from the restrictor conduit 50 to the annular region formed by the transfer conduit 52. This flow reversal further aids in the removal of kinetic energy.

The end of the restrictor conduit 50 is preferably disposed very close to the impactor 54 so that there is a minimum distance between the restrictor conduit 50 and the impactor 54. In this way, the target compound will be deposited generally on the forward surface 56 of the impactor 54. As shown in FIG. 3, the end of the transfer conduit 52 is joined to the end of the micro LC column 36 in a butt connection via glass lined stainless steel union 58. Thus, the union 58 is disposed at the junction between the restrictor conduit 50, the transfer conduit 52 and the micro LC column 36, with the impactor 54 being interposed between each of these conduits at this junction. It should also be appreciated that this construction advantageously minimizes the distance between the point of decompression and the micro LC column 36. In one form of the present invention, the union 58 is a glass lined model VSU004 union from Scientific Glass Engineering ("SGE"), Austin, Tex., USA.

FIG. 3 also shows that the opposite end of the transfer conduit 52 is contained in a 3-way glass lined stainless steel tee 60. The transfer conduit 30 is connected to the lateral or vertically extending leg 62 of the tee 60 to permit the decompressed supercritical fluid (e.g., gaseous carbon dioxide) to escape from the restrictor interface and be vented from the system or, alternatively, to be conveyed to a separate chromatographic system in order to detect any components which may not have been trapped by the interface 26. The tee 60 also supports the restrictor conduit 50 at leg 64 in coaxial alignment with the transfer conduit 52. In one form of the present invention, the tee 60 is a glass lined model VSUT004 tee from SGE. This particular tee is equipped with graphite-vespel ferrules and connectors for providing a seal between the tee 60 and the tubes. A deactivated fused silica sleeve 66 (e.g. 3.5 cm × 200 μm when the transfer conduit outer diameter is 150 μm) may also be coaxially disposed in the tee 60 to minimize any dead space in the tee.

In the event that any unwanted material accumulates on the impactor 54 or the micro LC column 36 which is not soluable in the fluid delivered to the restrictor interface 26 by the micro LC pump 34, it may be desirable to flush the restrictor interface and the micro LC column with a solvent capable of removing this unwanted material (e.g., methylene chloride). Additionally, it may be desirerable in the appropriate application to provide a method of cooling the restrictor interface to assist the trapping of the target compound and minimize any broadening of the chromatogram peaks by passing liquid nitrogen or carbon dioxide. In this regard, it should be noted that the transition from supercritical fluid to gas will create a cooling effect (Juoule-Thompson), which should aid in keeping the analytes in a narrow band. In any event, the need for additional cooling is substantially minimized by the use of a porous ceramic frit for the impactor due to its large surface area.

It will be appreciated that the above disclosed embodiment is well calculated to achieve the aforementioned objectives of the present invention. In addition, it is evident that those skilled in the art, once given the benefit of the foregoing disclosure, may now make modifications of the specific embodiment described herein without departing from the spirit of the present invention. Such modifications are to be considered within the scope of the present invention which is limited solely by the scope of the spirit of the appended claims.

What is claimed is:

1. An on-line supercritical fluid extraction chromatographic system, comprising:
   a means for providing a supercritical fluid flow;
   a cell means for extracting a target compound from a sample in said supercritical fluid flow;
   an interface means for trapping said extracted target compound while decompressing said supercritical fluid and venting said decompressed supercritical fluid from said system, wherein said interface means comprises:
   a first passage means for receiving said extracted target compound in said supercritical fluid flow;
   an impactor means associated with an output end of said first passage means for trapping said target compound concomitantly with a decompression of said supercritical fluid; and
   a second passage means in fluid communication with said output end of said first passage means for permitting said supercritical fluid to decompress and to be vented from said interface means;
   a means for causing a solvent to flow through said interface means after said target compound has been trapped to wash said trapped target compound from said interface means;
   a chromatographic means for separating and detecting a constituent of interest from said target compound entrained with said solvent flow.

2. An on-line supercritical fluid extraction multidimensional chromatographic system, comprising:
   a first conveying means for providing supercritical fluid flow at a controlled pressure;
   an extraction cell means, in fluid communication with said first conveying means, for holding a sample having target components that are soluble in said supercritical fluid, and for enabling said target components to be extracted from said sample in said supercritical fluid flow;

a second conveying means for providing solvent fluid flow for liquid chromatographic separation and detection;

a first valve means for controlling the direction of fluid flow from said extraction cell means and said second conveying means;

an interface means, in fluid communication with said first valve means, for trapping said extracted target component while decompressing said supercritical fluid, said interface means comprising:

a first passage means for receiving said extracted target compound in said supercritical fluid flow;

an impactor means associated with an output end of said first passage means for trapping said target compound concomitantly with a decompression of said supercritical fluid; and a second passage means in fluid communication with said output end of said first passage means for permitting said supercritical fluid to decompress and to be vented from said interface;

a liquid chromatographic means in fluid communication with said interface means for providing separation and detection of constituents of interest from said extracted target components via solvent fluid flow from said second conveying means, said first valve means being operative to direct said solvent fluid flow through said impactor means after said extracted target component has been trapped;

a second valve means for controlling the direction of fluid flow from said liquid chromatographic means; and a gas chromatographic means, in fluid communication with said second valve means, for analyzing said constituent of interest detected by said liquid chromatographic means.

3. The invention according to claim 2, wherein said impactor means is a porous ceramic frit.

4. The invention according to claim 3, wherein said porous ceramic frit is positioned at one end of a transfer conduit, and said first passage means includes a restrictor conduit which is coaxially disposed in said transfer conduit.

5. The invention according to claim 4, wherein said liquid chromatographic means comprises a micro LC column which is axially aligned to and in contact with the end of the transfer conduit containing the porous ceramic frit.

6. The invention according to claim 2 wherein said system includes a porous means interposed between said extraction cell means and said first valve means for filtering fluid flow from said extraction cell means.

7. The invention according to claim 2, wherein the second passage means is in fluid communication with a chromatographic means for detecting any components not removed from the decompressed supercritical fluid by the interface means.

* * * * *